United States Patent [19]

Nowack et al.

[11] Patent Number: 5,085,844

[45] Date of Patent: Feb. 4, 1992

[54] SORPTION OF TRIALKYL ARSINES

[75] Inventors: Gerhard P. Nowack; Tin-Tack P. Cheung, both of Bartlesville, Okla.

[73] Assignee: Phillips Petroleum Company, Bartlesville, Okla.

[21] Appl. No.: 619,166

[22] Filed: Nov. 28, 1990

[51] Int. Cl.$^5$ .................. B01D 53/14; C07C 7/12
[52] U.S. Cl. ................. 423/245.1; 423/210; 585/823
[58] Field of Search ............. 423/245.1, 210, 562; 556/64; 208/293, 295, 251 R; 585/820, 823; 55/72

[56] References Cited

U.S. PATENT DOCUMENTS

| | | | |
|---|---|---|---|
| 2,854,399 | 9/1958 | Weller | 208/293 |
| 3,804,750 | 4/1974 | Myers et al. | 208/253 |
| 3,876,533 | 4/1975 | Myers | 208/251 H |
| 3,933,624 | 1/1976 | Myers | 208/253 |
| 4,046,674 | 9/1977 | Young | 208/251 M |
| 4,101,631 | 7/1978 | Ambrosini et al. | 55/72 |
| 4,446,006 | 5/1984 | Albertson | 208/251 R |
| 4,474,896 | 10/1984 | Chao | 55/74 |
| 4,551,237 | 11/1985 | Fenton | 208/293 |
| 4,593,148 | 6/1986 | Johnson et al. | 585/823 |
| 4,605,812 | 8/1986 | Nowack et al. | 585/845 |
| 4,839,029 | 6/1989 | Ichikawa et al. | 208/251 H |
| 4,861,939 | 8/1989 | Debras et al. | 423/210 |
| 4,877,515 | 10/1989 | Audeh | 208/293 |
| 4,911,825 | 3/1990 | Roussel jet al. | 423/210 |
| 4,933,159 | 6/1990 | Nowack et al. | 423/245.1 |
| 4,971,608 | 11/1990 | Tooley et al. | 55/73 |

FOREIGN PATENT DOCUMENTS 60-68034 9/1983 Japan.

OTHER PUBLICATIONS

Zingaro et al., "Group V Oxides and Chalcogenides:..." Inorganic Chemistry, vol. 1, 1962, pp. 771–774.
Farlow et al., "1-Thiosorbitol", Journal of the American Chemical Society, vol. 70, 1948, pp. 1392 and 1393.

Primary Examiner—Gregory A. Heller
Assistant Examiner—Peter DiMauro
Attorney, Agent, or Firm—K. K. Brandes

[57] ABSTRACT

Trialkyl arsine (in particular trimethyl arsine) is removed from a fluid (e.g., a hydrocarbon-containing gas) by contacting the fluid with a sorbent material comprising (a) elemental sulfur, and (b) an inorganic support material, preferably alumina and/or silica and/or titania and/or activated carbon.

22 Claims, No Drawings

SORPTION OF TRIALKYL ARSINES

BACKGROUND OF THE INVENTION

This invention relates to the removal of trialkyl arsines from fluids by means of solid sorbents. In another aspect, this invention relates to the removal of trialkyl arsines from gases, in particular hydrocarbon-containing gases.

Materials for adsorbing and/or absorbing unsubstituted arsine ($AsH_3$) are well known. However, many of these materials are ineffective for the sorption of trialkyl arsines, which may be present as undesirable impurities in natural gas streams produced at some well sites. The present invention provides a sorbent material which is effective for removing trialkyl arsines from fluids by sorption (i.e., adsorption and/or absorption).

SUMMARY OF THE INVENTION

It is an object of this invention to provide a process for removing trialkyl arsines from fluids. It is another object of this invention to provide a process for removing trialkyl arsines from gases, in particular hydrocarbon-containing gases. Other objects will become apparent from the detailed description of the invention and the appended claims.

In accordance with this invention, a process for at least partially removing trialkyl arsines from fluids (preferably gases) comprises the step of contacting a fluid feed which contains at least one trialkyl arsine with a solid sorbent material comprising (preferably consisting essentially of) (a) elemental sulfur and (b) an inorganic support material (preferably selected from the group consisting of alumina, fluorided alumina, aluminum phosphate, magnesia, silica, aluminosilicates (such as clays and zeolites), titania, zirconia, hafnia, zinc oxide, zinc aluminate, aluminates of metals of Group IIA of the Periodic Table [as defined on page 852 of Webster's New Collegiate Dictionary, 1977], zinc titanate, titanates of Group IIA metals, activated carbon, and mixtures of the above materials); wherein said contacting is carried out at such contacting conditions as to obtain a fluid product having a lower trialkyl arsine content than said feed (with the spent sorbent material containing the portion of trialkyl arsine which has been removed from the feed).

DETAILED DESCRIPTION OF THE INVENTION

The term "trialkyl arsine", as used herein, refers to compounds having the general chemical formula of $R_3As$, wherein each R is a radical independently selected from among alkyl groups (straight and/or branched), preferably having 1-6 (more preferably 1-3) carbon atoms. Particularly preferred trialkyl arsines are trimethyl arsine, triethyl arsine, dimethyl ethyl arsine and diethyl methyl arsine.

Any suitable liquid or gaseous fluid stream which contains trialkyl arsine(s) can be used as feed in the process of this invention. Preferably, the feed is gaseous. Non-limiting examples of suitable feeds are: natural gas; gaseous petroleum fractions comprising paraffins and olefins containing 1-6 carbon atoms per molecule; and gaseous products from thermal and catalytic cracking of petroleum, shale oil or coal. Generally, the gases comprise methane, ethane, ethylene, propane, propylene, n-butane, isobutane, butenes; and the like. These gas streams can contain other impurities, such as hydrogen sulfide, carbonyl sulfide (COS), mercaptans, organic sulfides, mercury and/or compounds thereof, carbon monoxide, carbon dioxide, inert gases ($N_2$, He, Ne, Ar), and the like.

Other arsenic compounds may also be present in the fluid stream which is treated by the process of this invention, such as $AsH_3$, $RAsH_2$, $R_2AsH$, and the like, wherein R is an alkyl group, as defined above. It is also possible to have triphenyl arsine, dialkyl phenyl arsines, dialkyl cycloalkyl arsines, and the like present in the feed. Preferably, free oxygen is substantially absent from the feed.

Generally, the total concentration of the trialkyl arsine(s) in the feed (preferably gaseous) is in the range of from about 1 ppb As (1 part by weight of arsenic per billion parts by weight of feed) to about 0.1 weight-% As, preferably about 0.01-10 ppm As (parts by weight of arsenic per million parts by weight of feed). The concentrations of the other impurities and the exact composition of the feed will widely vary from feedstock to feedstock.

The sorbent materials which are used in the process of this invention comprise elemental sulfur and an inorganic support material. Generally the sulfur content in the sorbent is in the range of from about 1 to about 50, preferably from about 3 to about 25, weight-% elemental S. It is within the scope of this invention to have metal oxides and/or metal sulfur compounds (such as Fe(III) oxide and/or sulfite and/or sulfate or the corresponding compounds of Co or Ni or Mn or mixtures thereof) present (besides elemental sulfur) in the sorbent material.

Any suitable, effective inorganic support material can be employed as component (b). Preferably, the support material is selected from the group consisting of alumina, fluorided alumina (i.e., alumina which has been treated with HF or $NH_4HF_2$ under such conditions as to incorporate fluoride ions into the crystal lattice of alumina), aluminum phosphate, magnesia (MgO), silica, titania ($TiO_2$), zirconia ($ZrO_2$), hafnia ($HfO_2$), zinc oxide, zinc aluminate ($ZnAl_2O_4$) aluminates of Group IIA metals (i.e., of Be, Mg, Ca, Sr, Ba), zinc titanate ($Zn_2TiO_4$), titanates of Group IIA metals, activated carbon, and mixtures of two or more than two of the above materials. Presently more preferred support materials are alumina, silica, titania, activated carbon, and mixtures of two or more of these materials.

The elemental sulfur component (a) can be combined with the inorganic support material (b) in any suitable manner, such as by impregnating or spraying the support material with a solution of sulfur (e.g., in carbon disulfide or another effective solvent for sulfur), followed by drying of the sulfur-containing material; or by impregnating the support material with molten sulfur; or by subliming sulfur onto the support material; or by depositing Fe(III) sulfide ($Fe_2S_3$) or at least one polysulfide of a transition metal, such as Mn, Fe, Co, Ni, Cu, or mixtures thereof, preferably $Fe_2(S_3)_3$, on the support material, and then at least partially converting the transition metal polysulfide to elemental sulfur, preferably by reaction with a free oxygen containing gas (e.g., air), more preferably during drying. The preparation of the transition metal polysulfides can be carried out substantially in accordance with the procedure described in the Journal of the American Chemical Society 70, 1948, page 1393, left column.

The sorbent particles of this invention can have any suitable surface area (preferably about 10–1000 m$^2$/g, as measured by the B.E.T. method employing N$_2$), any suitable shape (such as spherical, cylindrical, ring-shaped, trilobal etc.), and any suitable size (such as about 0.2–20 mm diameter for spherical particles).

Any suitable contacting conditions can be employed in the sorption process of this invention. Generally, the temperature in the contacting zone is in the range of from about −20 to about 100° C., preferably about 20 to about 50° C. Generally, the pressure in the contacting zone is in the range of from about 1 to about 500 atm., preferably about 1 to about 70 atm. Generally, the gas hourly space velocity of the gaseous feed in the contacting zone is in the range of from about 10 to about 20,000 volume of feed/volume of sorbent/hour, preferably about 1,000 to about 10,000 volume/volume/hour, measured at about 25° C./1 atm. Generally, the contacting is continued until trialkyl arsine breakthrough occurs, i.e., when the treated product contains more trialkyl arsines than can be tolerated, such as about 50 ppb.

Treatment of the feed streams in accordance with the process of this invention can be carried out in any suitable manner. For example, in a preferred embodiment a bed of the sorbent is placed as a fixed bed in a confined zone, and a fluid stream (preferably a gas) is passed therethrough in either upward or downward flow. Other suitable, yet less preferred methods of treatment can include a fluidized operation in which the feed and the sorbent particles are maintained in a state of turbulence under hindered settling conditions in a confined zone, moving bed operations in which the sorbent passes as a moving bed countercurrently to or concurrently with the feed, etc. In a fixed bed operation of a continuous process, the flow of fluid can be rotated between two or more sorbent beds with at least one being in regular operation, the other being in a regeneration mode. Continuous processes are preferred, but it is understood that batch type operations can be employed when desired.

It is within the scope of this invention to employ a combination of sorbents, such as a first bed (guard bed) of a supported CuO-ZnO material (described in U.S. Pat. No. 4,593,148) or PbO/Al$_2$O$_3$ for substantial removal of AsH$_3$ and/or H$_2$S from the feed, and at least one subsequent downstream bed containing the sorbent material of this invention for absorbing trialkyl arsines. This multi-bed operation can be carried out in one reactor containing a layer of the supported CuO-ZnO material or PbO/Al$_2$O$_3$ (or any other known sorbent for AsH$_3$ and H$_2$S) and a downstream layer of a trialkyl arsine sorbent of this invention. Or the multi-bed operation can be carried out using two (or more) separate sorption reactors: a first reactor containing the supported CuO-ZnO material or PbO/Al$_2$O$_3$ (or any other known sorbent for AsH$_3$ and H$_2$S) and a second reactor containing the trialkyl arsine sorbent of this invention, wherein the feed passes through the first reactor and thereafter through the second reactor.

The process of this invention will be further illustrated by the following non-limiting examples.

EXAMPLE I

This example illustrates the experimental setup for investigating the absorption of trimethyl arsine by sorbent materials.

A nitrogen gas stream was passed through a flask containing liquid trimethyl arsine (provided by Strem Chemicals, Inc.), which was cooled to about −78° C. by placing the flask in a dry ice/acetone mixture. The gas stream, which contained N$_2$ and trimethyl arsine, was passed through a glass tube of about 7 mm diameter and about 12 cm length containing about 5 grams of one of the sorbents described below. The gas which exited from the absorption tube was passed through an aqueous solution of KMnO$_4$ and then to a flow meter. The flow rate of the gas was about 1800 cc/hour (equivalent to about 360 cc/cc sorbent/hour).

When trimethyl arsine breakthrough occured (i.e., when the sorbent had reached its maximum arsine absorption capacity), the purple color of the KMnO$_4$ solution turned brownish. After arsine breakthrough had been detected, the flow of the trimethyl arsine containing gas stream was stopped, and a purge stream of pure nitrogen was passed through the sorbent material for about 15 hours so as to purge unabsorbed trimethyl arsine therefrom. The absorption tube containing the sorbent and absorbed trimethyl arsine was weighed. The difference between this weight and the initial weight of the tube with fresh sorbent was the weight of absorbed trimethyl arsine.

EXAMPLE II

This example illustrates the preparation of several absorbents and their capacity for trimethyl arsine sorption.

Sorbent A was sulfur-impregnated alumina containing about 3.3 weight-% S. A 20–40 mesh sample of 1.11 grams of Harshaw Al-3996R alumina (provided by Engelhard Corporation, Edison, NJ) was impregnated with a solution of 0.038 grams of elemental sulfur dissolved in about 1 cc carbon disulfide (CS$_2$). The obtained yellow-colored material was partially dried at room temperature. This partially dried material was placed into a tube, and a stream of N$_2$ was passed through the material.

Sorbent B was a sulfur-impregnated alumina sorbent material which contained 4.8 weight-% S. A sample of 5 grams of 20–40 mesh Alcoa S-201 alumina (provided by Aluminum Company of America, Pittsburgh, PA) was impregnated with a solution of 0.25 grams sublimed sulfur in about 8 cc CS$_2$, followed by drying and purging with N$_2$ (as described for Sorbent A).

Sorbent C was sulfur-impregnated silica containing 4.8 weight-% S. A sample of 3.8 grams of dried, 20–40 mesh silica (Davison Grade 59 silica, provided by Davison Chemical Division of W. R. Grace and Company, Baltimore, MD) was impregnated with a solution of 0.19 grams of sublimed sulfur in CS$_2$. The thus-impregnated material was dried and purged with N$_2$, substantially in accordance with the procedure for Sorbent A.

Sorbent D was sulfur-impregnated titania containing 3.4 weight-% S. A sample of 4.6 grams of 20–40 mesh titania (Calsicat 47D-26A titania, provided by Mallinckrodt, Inc., St. Louis, MO) was impregnated with a solution of 0.16 grams of elemental sulfur in CS$_2$. The thus-impregnated material was dried and purged with N$_2$, substantially in accordance with the procedure for Sorbent A.

Sorbent E was sulfur-impregnated activated carbon containing 5 weight-% S. A sample of 2.83 grams of 20–40 mesh dried charcoal, which had been heated at 150° C. overnight, was impregnated with a solution of 0.15 grams of sublimed sulfur in CS$_2$. The thus-impregnated material was dried and purged with N$_2$, substantially in accordance with the procedure for Sorbent A.

Sorbent F was an alumina material which contained elemental sulfur and sulfur compounds of iron. Alumina extrudates (provided by Engelhard Corporation, Edison, NJ, under the product designation "Harshaw Al-3996R") were impregnated with enough of an 0.5 molar aqueous $FeCl_3$ solution to provide an iron content of about 9 weight-% Fe (based on the weight of dry Sorbent F). The $FeCl_3$-impregnated alumina was dried and then impregnated with a 0.5 molar aqueous solution of $Na_2S_3$ (prepared by mixing an aqueous solution of $Na_2S$ and elemental sulfur at a 1:3 molar ratio) so as to provide a sulfur content of about 22 weight-% S (based on the weight of dry Sorbent F). The black material, which initially contained $Fe_2(S_3)_3$ (iron(III) polysulfide), turned yellow-brown upon drying in air. The air-dried material was crushed and sieved, and a 20-40 mesh sample was used for trimethyl arsine sorption. X-ray photoelectron spectroscopy analysis (by means of a PHI-550 ESCA/Auger spectrometer equipped with an aluminum X-ray source) of a material similar to air-dried Sorbent F did not reveal the presence of $Fe_2(S_3)_3$ but indicated that the material comprised a mixture of elemental sulfur, $Fe_2O_3$, $Fe_2(SO_3)_3$ and $Fe_2(SO_4)_3$ on alumina.

Trimethyl arsine tests were carried out with Sorbents A-F in accordance with the procedure described in Example I. Test results, summarized in the Table below, demonstrate that the supported sulfur materials are quite effective as trialkyl arsine sorbents. Additional tests (not described in detail herein) indicated that unimpregnated $Al_2O_3$, $SiO_2$ and $TiO_2$ did not absorb any trimethyl arsine.

TABLE

| Sorbent | Run Time | Absorbed As (Wt. %) |
|---|---|---|
| A ($S/Al_2O_3$) | until As breakthrough | 4.4 |
| B ($S/Al_2O_3$) | several hours[1] | 1.7 |
| C ($S/SiO_2$) | several hours[1] | 2.6 |
| D ($S/TiO_2$) | several hours[1] | 0.9 |
| E (S/activ. C) | several hours[1] | 6.3 |
| F ($S/FeS_xO_y/Al_2O_3$) | several hours[1] | 3.4 |

[1]trimethyl arsine breakthrough had not yet occurred.

Further tests (not described in detail herein) revealed that alumina-supported Fe(III) sulfide ($Fe_2S_3$) and polysulfides of Co and Mn ($CoS_3$; $MnS_3$), all of which had been exposed to air during drying and are believed to have been oxidized to elemental sulfur and oxygen-containing compounds of Fe, Co and Mn, respectively, also absorbed trimethyl arsine (approximately 1-3 weight-% As).

EXAMPLE III

Two sulfur-containing alumina sorbent materials which were substantially the same as Sorbents A and F were field-tested at a commercial natural gas compressor station near Roswell, NM. The natural gas contained about 0.5 ppm As, primarily as trimethyl arsine. The stainless steel absorption tubes used in these field tests had a diameter of 0.5 inch, were 3 feet long, and contained about 70 cc (about 71 g) of the sorbent material. Treatment of the natural gas with each of the two sorbent materials removed in excess of 99% of the trimethyl arsine present in the gas.

Reasonable variations and modifications which will be apparent to those skilled in the art, can be made within the scope of the disclosure and appended claims without departing from the scope of this invention.

That which is claimed is:

1. A process for at least partially removing trialkyl arsines from gases comprising the step of contacting a gaseous feed which contains at least one trialkyl arsine with a solid sorbent material comprising (a) elemental sulfur and (b) an inorganic support material; wherein said contacting is carried out at such contacting conditions as to obtain a product having a lower trialkyl arsine content than said feed; wherein the content of said at least one trialkyl arsine in said feed is such as to provide a level of about 1 ppb to about 0.1 weight-% As; and wherein said sorbent has been prepared by depositing at least one polysulfide of at least one transition metal selected from the group consisting of manganese, iron, cobalt, nickel and copper on said inorganic support material, and at least partially converting said at least one polysulfide to elemental sulfur by reaction with a free oxygen containing gas.

2. A process in accordance with claim 1, wherein said feed is a hydrocarbon-containing gas.

3. A process in accordance with claim 1, wherein said trialkyl arsine has the chemical formula of $R_3As$ with each R being independently selected from the group consisting of alkyl groups containing 1-6 carbon atoms.

4. A process in accordance with claim 3, wherein said alkyl groups contain 1-3 carbon atoms.

5. A process in accordance with claim 1, wherein said at least one trialkyl arsine is selected from the group consisting of trimethyl arsine, triethyl arsine, dimethyl ethyl arsine and diethyl methyl arsine.

6. A process in accordance with claim 1, wherein said feed contains about 0.01-10 ppm arsenic.

7. A process in accordance with claim 1, wherein said sorbent material contains about 1-50 weight-% elemental sulfur.

8. A process in accordance with claim 1, wherein component (b) of said sorbent material is selected from the group consisting of alumina, fluorided alumina, aluminum phosphate, silica, aluminosilicates, magnesia, titania, zirconia, hafnia, zinc oxide, zinc aluminate, aluminates of metals of Group IIA of the Periodic Table, zinc titanate, titanates of Group IIA metals, activated carbon, and mixtures thereof.

9. A process in accordance with claim 8, wherein component (b) of said sorbent material is selected from the group consisting of alumina, silica, titania, activated carbon and mixtures thereof.

10. A process in accordance with claim 1, wherein said sorbent material has been prepared by a method comprising the steps of impregnating alumina with a solution of an iron(III) compound and with a solution of sodium polysulfide so as to form iron(III) polysulfide on said alumina, and drying the thus impregnated alumina in the presence of a free oxygen containing gas under such conditions as to convert said iron(III) polysulfide to a mixture comprising elemental sulfur.

11. A process in accordance with claim 10, wherein said iron(III) compound is $FeCl_3$, said sodium polysulfide is $Na_2S_3$, and said iron(III) polysulfide is $Fe_2(S_3)_3$.

12. A process for at least partially removing trialkyl arsines from gases comprising the step of contacting a gaseous feed which contains at least one trialkyl arsine with a solid sorbent material consisting essentially of (a) elemental sulfur and (b) an inorganic support material; wherein said contacting is carried out at such contacting conditions as to obtain a product having a lower trialkyl arsine content than said feed, and the spent sorbent material contains that portion of said at least one trialkyl arsine which has been removed from said feed; and wherein the content of said at least one trialkyl arsine in said feed is such as to provide a level of about 1 ppb to about 0.1 weight-% As.

13. A process in accordance with claim 12, wherein said feed is a hydrocarbon-containing gas.

14. A process in accordance with claim 12, wherein said trialkyl arsine has the chemical formula of $R_3As$ with each R being independently selected from the group consisting of alkyl groups containing 1-6 carbon atoms.

15. A process in accordance with claim 14, wherein said alkyl groups contain 1-3 carbon atoms.

16. A process in accordance with claim 12, wherein said at least one trialkyl arsine is selected from the group consisting of trimethyl arsine, triethyl arsine, dimethyl ethyl arsine and diethyl methyl arsine.

17. A process in accordance with claim 12, wherein said feed contains about 0.01-10 ppm arsenic.

18. A process in accordance with claim 12, wherein said sorbent material contains about 1-50 weight-% elemental sulfur.

19. A process in accordance with claim 12, wherein component (b) of said sorbent material is selected from the group consisting of alumina, fluorided alumina, aluminum phosphate, silica, aluminosilicates, magnesia, titania, zirconia, hafnia, zinc oxide, zinc aluminate, aluminates of metals of Group IIA of the Periodic Table, zinc titanate, titauates of Group IIA metals, activated carbon, and mixtures thereof.

20. A process in accordance with claim 19, wherein component (b) of said sorbent material is selected from the group consisting of alumina, silica, titania, activated carbon and mixtures thereof.

21. A process in accordance with claim 20, wherein said sorbent material contains about 3-25 weight-% elemental sulfur.

22. A process in accordance with claim 12, wherein said sorbent material has been prepared by a process comprising impregnating said inorganic support material with elemental sulfur.

* * * * *